(12) United States Patent
Patek et al.

(10) Patent No.: US 11,058,818 B2
(45) Date of Patent: Jul. 13, 2021

(54) LQG ARTIFICIAL PANCREAS CONTROL SYSTEM AND RELATED METHOD

(71) Applicant: UNIVERSITY OF VIRGINIA PATENT FOUNDATION, Charlottesville, VA (US)

(72) Inventors: Stephen D. Patek, Charlottesville, VA (US); Marc D. Breton, Charlottesville, VA (US)

(73) Assignee: UNIVERSITY OF VIRGINIA PATENT FOUNDATION, Charlottesville, VA (US)

(*) Notice: Subject to any disclaimer, the term of this patent is extended or adjusted under 35 U.S.C. 154(b) by 226 days.

(21) Appl. No.: 16/205,398

(22) Filed: Nov. 30, 2018

(65) Prior Publication Data

US 2019/0099555 A1    Apr. 4, 2019

Related U.S. Application Data

(63) Continuation of application No. 12/665,420, filed as application No. PCT/US2008/067723 on Jun. 20, 2008, now Pat. No. 10,173,006.

(Continued)

(51) Int. Cl.
*A61M 5/172* (2006.01)
*G16H 50/20* (2018.01)
*G16H 40/63* (2018.01)
*G16H 10/40* (2018.01)
*G16H 20/60* (2018.01)
(Continued)

(52) U.S. Cl.
CPC ........... *A61M 5/1723* (2013.01); *G06F 19/00* (2013.01); *G16H 10/40* (2018.01); *G16H 20/17* (2018.01); *G16H 20/60* (2018.01); *G16H 40/63* (2018.01); *G16H 50/20* (2018.01); *G16H 50/50* (2018.01); *A61B 5/14532* (2013.01)

(58) Field of Classification Search
CPC ........ A61B 5/00; A61B 5/14532; A61M 5/14; A61M 5/1723; G06F 19/3456; G06F 19/00; G16H 50/20; G16H 50/50
See application file for complete search history.

(56) References Cited

U.S. PATENT DOCUMENTS 6,572,545 B2    6/2003  Knobbe et al.
6,575,905 B2    6/2003  Knobbe et al.
(Continued)

FOREIGN PATENT DOCUMENTS

WO    2006/124716 A2    11/2006
WO    2006/133348 A2    12/2006

OTHER PUBLICATIONS

The extended European Search Report dated Feb. 3, 2020, by the European Patent Office in corresponding European Application No. 19203101.1. (10 pages).

(Continued)

*Primary Examiner* — Eric J Messersmith
(74) *Attorney, Agent, or Firm* — Buchanan Ingersoll & Rooney PC

(57) ABSTRACT

The invention relates to a methods and systems for determining on insulin dosing insulin recommended. The invention employs Linear Quadratic methodology to determine the insulin dosing recommendation based on a patient's present physiological state, which is estimated by an adaptive filter methodology employing a dynamic model, which utilizes real-time measurements of blood glucose concentration.

14 Claims, 5 Drawing Sheets

Related U.S. Application Data

(60) Provisional application No. 60/964,667, filed on Aug. 14, 2007, provisional application No. 60/936,613, filed on Jun. 21, 2007.

(51) Int. Cl.
    *G16H 50/50*      (2018.01)
    *G06F 19/00*      (2018.01)
    *G16H 20/17*      (2018.01)
    *A61B 5/145*      (2006.01)

(56) References Cited

U.S. PATENT DOCUMENTS

| | | |
|---|---|---|
| 7,670,288 B2 | 3/2010 | Sher |
| 7,806,854 B2 | 10/2010 | Damiano et al. |
| 2003/0195404 A1 | 10/2003 | Knobbe et al. |
| 2006/0276771 A1 | 12/2006 | Galley et al. |

OTHER PUBLICATIONS

Bequette et al., "A Critical Assessment of Algorithms and Challenges in the Development of a Closed-Loop Artificial Pancreas", Diabetes Technology & Therapeutics, Feb. 1, 2005, pp. 28-47, vol. 7, No. 1, XP 055026508.

Office Action (Communication) dated Oct. 8, 2018, by the European Patent Office in corresponding European Patent Application No. 08780895.2. (9 pages).

Skelton and Shi, "The data-based LOG control problem," Decision and Control, 1994., Proceedings of the 33rd IEEE Conference on (vol. 2), 1994, 1447-1452.

The Control Handbook, William S. Levine, CRC Press LLC, Boca Raton, FL, 1996, CRC Press, 1995, ISBN: 0/8493-8570-9.

Patek et al., "Linear Quadratic Gaussian-Based Closed-Loop Control of Type 1 Diabetes," Journal of Diabetes Science and Technology, vol. 1, No. 6, pp. 834-841, Nov. 1, 2007.

LQG ARTIFICIAL PANCREAS CONTROL SYSTEM AND RELATED METHOD

CROSS-REFERENCES TO RELATED APPLICATIONS

This application claims benefit under 35 U.S.C. § 119(e) to U.S. Provisional Patent Application Ser. No. 60/936,613 filed on Jun. 21, 2007, and to United States Provisional Patent Application Ser. No. 60/964,667 filed on Aug. 14, 2007, which are hereby incorporated by reference in their entireties.

BACKGROUND OF THE INVENTION

In health, blood glucose (BG) is tightly controlled by a hormonal network that includes the gut, liver, pancreas, and brain, ensuring stable fasting BG levels (~80-100 mg/dl) and transient postprandial glucose fluctuations. Diabetes is a combination of disorders characterized by absent or impaired insulin action, resulting in hyperglycemia. Intensive insulin and oral medication treatment to maintain nearly normal levels of glycemia markedly reduces chronic complications in both Type 1 and Type 2 diabetes, but may cause a risk of potentially life-threatening severe hypoglycemia (SH). This SH results from imperfect insulin replacement, which may reduce warning symptoms and hormonal defenses. Consequently, hypoglycemia has been identified as the primary barrier to optimal diabetes management.

DESCRIPTION OF RELATED ART

Glucose control has been studied for more than 3 decades and widely different solutions have been proposed, though it is only very recently that technology and algorithm have come together to enable glucose control elsewhere than in the ICU of a hospital.

Information relevant to attempts to provide glucose control based on intravenous (IV) glucose measure and both positive (glucose) and negative (insulin) control actuation can be found in the following references, which are not admitted to be prior art with respect to the present invention by inclusion in this section:
(1) Pfeiffer E F, Thum Ch, and Clemens A H: The artificial beta cell—A continuous control of blood sugar by external regulation of insulin infusion (glucose controlled insulin infusion system). Horm Metab Res 487: 339-342, 1974; and
(2) Clemens A H: Feedback control dynamics for glucose controlled insulin infusion system. MedProg Technol 6: 91-98, 1979.

Both of these regulators were based on a proportional-integral-derivative strategy (PID): the injected insulin is proportional to the difference between a fixed plasma glucose target and the measured plasma glucose as well as to the rate of change of plasma glucose. However, each one of these reference suffers from the following disadvantage, which are not admitted to have been known in the art by inclusion in this section:
(1) PID control is not "model-based." In other words, prediction plays no role in computing control actions; and
(2) PID control actions are computed merely as a simple linear function of the error signal.

Information relevant to attempts to provide glucose control based on prediction of glucose level can be found in the following references, which are not admitted to be prior art with respect to the present invention by inclusion in this section:
(1) Albisser A M, Leibel B S, Ewart T G, Davidovac Z, Botz C K, and Zingg W: An artificial endocrine pancreas. Diabetes, 23: 389-396, 1974;
(2) Marliss E B, Murray F T, Stokes E F, Zinman B, Nakhooda A F, Denoga A, Leibel B S, and Albisser A M: Normalization of glycemia in diabetics during meals with insulin and glucagon delivery by the artificial pancreas. Diabetes 26: 663-672, 1977;
(3) Kraegen E W, Campbell L V, Chia Y O, Meler H, and Lazarus L: Control of blood glucose in diabetics using an artificial pancreas. Aust N Z J Med 7: 280-286, 1977;
(4) Fischer U, Jutzi E, Freyse E-J, and Salzsieder E: Derivation and experimental proof of a new algorithm for the artificial r-cell based on the individual analysis of the physiological insulin-glucose relationship. Endokrinologie 71:65-75, 1978; and
(5) Broekhuyse H M, Nelson J D, Zinman B, and Albisser A M: Comparison of algorithms for the closed-loop control of blood glucose using the artificial beta cell. IEEE Trans Biomed Eng BME-28: 678-687, 1981.

Providing glucose control based on prediction of glucose level tends to counteract the inherent inertia of exogenous insulin compared to the endogenous hormones. However, each one of these reference suffers from one or more of the following disadvantages, which are not admitted to have been known in the art by inclusion in this section:
(1) Since a new control profile is computed for each CGM reading based on predictions, Model Predictive Control (MPC) is much more computationally demanding than PID;
(2) The frequency of control updates may be limited by the computational capacity of the platform on which the control is implemented; and
(3) Inaccuracy in the predictive model results in poor glucose control.

Information relevant to attempts to provide glucose control, spanning a broader range of control theory, can be found in the following references, which are not admitted to be prior art with respect to the present invention by inclusion in this section:
(1) Salzsieder E, Albrecht G, Fischer U, and Freyse E-J: Kinetic modeling of the glucoregulatory system to improve insulin therapy. IEEE Trans Biomed Eng 32: 846-855, 1985;
(2) Fischer U, Schenk W, Salzsieder E, Albrecht G, Abel P, and Freyse E-J: Does physiological blood glucose control require an adaptive strategy? IEEE Trans Biomed Eng BME-34:575-582, 1987;
(3) Sorensen JT: A Physiologic Model of Glucose Metabolism in Man and its Use to Design and Assess Improved Insulin Therapies for Diabetes, Ph.D. dissertation, Department of Chemical Engineering, MIT, 1985;
(4) Swan G W: An optimal control model of diabetes mellitus. Bull Math Bio 44: 793-808, 1982;
(5) Fisher M E and Teo K L: Optimal insulin infusion resulting from a mathematical model of blood glucose dynamics. IEEE Trans Biomed Eng 36: 479-486, 1989;
(6) Ollerton R L: Application of optimal control theory to diabetes mellitus. Int J Control 50: 2503-2522, 1989;
(7) Fisher M E: A semi closed-loop algorithm for the control of blood glucose levels in diabetics. IEEE Trans Biomed Eng 38: 57-61, 1991; and (8) Kienitz K H and Yoneyama T: A robust controller for insulin pumps based on H-infinity theory. IEEE Trans Biomed Eng 40: 1133-1137, 1993.

However, each one of these reference suffers from one or more of the following disadvantages, which are not admitted to have been known in the art by inclusion in this section:
(1) all were concerned with IV sensing, and IV action; and
(2) most relied on some approximate modeling of human physiology.

Attempts have also been made to provide glucose control based on self-monitoring of blood glucose (SMBG) to adjust the dosing of insulin delivered via injections or insulin pump. However, such attempts to provide glucose control suffer from many disadvantages, which are not admitted to have been known in the art by inclusion in this section. Glucose is measured at infrequent (<5/day) and irregular times during the day and insulin is injected subcutaneously according to both these measures and the estimated amount of carbohydrates ingested. Depending on the treatment strategy, the insulin is either injected continuously (basal rate) or discretely (boluses) via a pump, or only discretely, via injections containing both fast acting and long acting insulin. In both cases therelation between the amount of insulin injected and the measured plasma glucose is determined by the care practitioner and the patient based on past experience and initial rule of thumbs (1800-rule and 450-rule). Insulin boluses are traditionally calculated in two phases: First, the amount of insulin is computed that is needed by a person to compensate for the carbohydrate content of an incoming meal. This is done by estimating the amount of carbohydrates to be ingested and multiplying by each person's insulin/carbohydrate ratio. Second, the distance between actual blood glucose (BG) concentration and individual target level is calculated and the amount of insulin to reach target the target is computed. This is done by multiplying the (BG—target) difference by an individual insulin correction factor. It is therefore evident that a good assessment of each person's carbohydrate ratio and correction factor is critical for the optimal control of diabetes.

Attempts have been made to develop regulation systems (e.g. artificial pancreas) to control insulin delivery in people with diabetes based on observing and acting upon the glucose/insulin levels using real-time measurements at sampling frequencies less than or equal to 5 minutes. Some control efforts have focused on the Subcutaneous-Subcutaneous (SC-SC) route as it is the most likely to be easily mass marketed and it relies on readily available technologies. However, each one of these technologies suffer from one or more of the following disadvantages, which are not admitted to have been known in the art by inclusion in this section:
(1) The continuous sensors currently available experience delays estimated between 10 and 20 minutes.
(2) The continuous sensors' accuracy is still lower than for example finger stick measurement (SMBG) and therefore none of the currently available sensors have been approved for 'replacement' by the Food & Drug Administration (FDA), therefore precluding their use as such in clinical decision.
(3) Subcutaneous injection of insulin imposes an additional actuation delay, the exogenous insulin being first transported from the injection site to the central vascular system and only then following the pathway of exogenous IV injected insulin.

Information relevant to attempts to provide glucose control based on implantable sensors and insulin pumps can be found in the following references, which are not admitted to be prior art with respect to the present invention by inclusion in this section:
(1) Leblanc H, Chauvet D, Lombrail P, Robert J J: Glycemic control with closed-loop intraperitoneal insulin in type I diabetes. Diabetes Care, 9: 124-128, 1986;
(2) J L Selam, P Micossi, F L Dunn, and D M Nathan: Clinical trial of programmable implantable insulin pump for type I diabetes, Diabetes Care 15: 877-885, 1992;
(3) E Renard: Implantable closed-loop glucose-sensing and insulin delivery: the future for insulin pump therapy, Current Opinion in Pharmacology, 2(6), 708-716, 2002; and
(4) R. Hovorka: Continuous glucose monitoring and closed-loop systems Diabetic Medicine 23 (1), 1-12, 2006.

The sensors are implantable directly into an artery, and were believed to be closer to IV sensing, and therefore less inclined to delays and errors. However, recent studies have shown that these sensors suffer from delays equivalent to SC sensors, even though the implantable sensors sample blood directly. Additionally, these attempts suffer from one or more of the following disadvantages, which are not admitted to have been known in the art by inclusion in this section:
(1) Surgery is required to insert the technologies;
(2) The implanted devices have a limited life time, from 3 to 18 months; and
(3) Despite expectations that implantable pumps would be more efficient than SC pumps, because they more closely mimic natural peritoneal injection of insulin, the technologies suffer from insulin aggregation.

Information relevant to attempts to regulate glucose homeostasis have can be found in the following references, which are not admitted to be prior art with respect to the present invention by inclusion in this section:
(1) El-Khatib F H, Jiang J, Damiano E R: Adaptive closed-loop control provides blood-glucose regulation using dual subcutaneous insulin and glucagon infusion in diabetic swine. Diabetes Sci Tech, 1:181-192, 2007;
(2) Hovorka R., Canonico V., Chassin L. J., Haueter U., Massi-Benedetti M., Federici M. O., Pieber T. R., Schaller H. C., Schaupp L., Vering T.: Nonlinear model predictive control of glucose concentration in subjects with type 1 diabetes. Phsyiological Measurement, 25 (4) 905-920, 2004; and
(3) Steil G M, Rebrin K, Darwin C, Hariri F, Saad M F: Feasibility of automating insulin delivery for the treatment of type 1 diabetes. Diabetes. December; 55(12): 3344-50, 2006.

Information relevant to Linear Quadratic Gaussian (LQG) control methodology, can be found in the following reference, which is not admitted to be prior art with respect to the present invention by inclusion in this section: B. D. O. Anderson and J. B. Moore. Optimal Control: Linear Quadratic Methods. Prentice-Hall, Englewood Cliffs, N.J. 1989. The LQG control problem lies within a larger class of control design methodologies, including discrete-time Markovian control problems and robust control. Information relevant to discrete-time Markovian control problems can be found in the following references, which are not admitted to be prior art with respect to the present invention by inclusion in this section:
(1) S. D. Patek, Partially Observed Stochastic Shortest Path Problems with Approximate Solution by Neuro-Dynamic Programming, IEEE Transactions on Systems, Man, and Cybernetics, in Press;

(2) S. D. Patek, Policy Iteration Type Algorithms for Recurrent State Markov Decision Processes, Computers and Operations Research, 31(14), December 2004, 2333-2347, 2004;

(3) S. D. Patek, On Terminating Markov Decision Processes with a Risk Averse Objective Function, Automatica, 37(9), September 2001, 1379-1386, 2001; and (4) E. Campos-Nanez and S. D. Patek, Dynamically Identifying Regenerative Cycles in Simulation-Based Optimization Algorithms for Markov Chains, IEEE Transactions on Automatic Control, 49(4), June 2004, 1022-1025, 2004.

Information relevant to robust control problems can be found in the following references, which are not admitted to be prior art with respect to the present invention by inclusion in this section:

(1) J. W. Kamman, S. D. Patek, and S. A. Hoeckley, Application of Multivariable Linear Control Design to Marine Towed Systems, AIAA Journal of Guidance Control, and Dyanmics, 19(6), 1246-1251, 1996; and (2) S. D. Patek and M. Athans, Optimal Robust H. Control, IEEE Conference on Decision and Control (CDC 1994), New York, December 1994, 3539-3544, 1994.

For the foregoing reasons, there remains a need for a system to compute optimal insulin injection dosage amounts based on continuous glucose monitoring.

BRIEF SUMMARY OF THE INVENTION

Versions of the present invention relate to a method for determining an insulin dosing recommendation. The method comprises applying an adaptive filter scheme to estimate a present physiological state of a patient based on real-time measurements of blood glucose concentration in the patient, wherein the adaptive filter scheme models the present physiological state of the patient using a dynamic model. The method further comprises using Linear Quadratic methodology to determine an insulin dosing recommendation based on the present physiological state so estimated. According to particularly preferred versions of the invention, the insulin dosing recommendation is defined as a Linear combination of a gain vector (S) and a state vector (X), so as to minimize a quadratic cost function.

According to preferred versions of the method, the dynamic model is an augmented minimal model of glucose kinetics, an augmented reduced meal model, or an augmented meal model.

According to preferred versions of the method, the dynamic model employs a plurality of physiological parameters, and the method further comprises an initial step of customizing the dynamic model by fixing at least one physiological parameter.

According to other preferred versions of the method, at least one physiological parameter is fixed at an average value, wherein the average value represents an average of values measured for a plurality of subjects. In these versions, it is particularly preferred that at least one physiological parameter is modified based on measurements of blood glucose concentration and blood insulin concentration from the patient to ensure absence of bias between an estimated and an actual plasma glucose concentration at steady state.

According to preferred versions of the method, the method further comprises determining an optimal gain for the dynamic model.

According to preferred versions of the method, the dynamic model is optimized using a Kalman filter, or an extended Kalman filter.

According to a particularly preferred version of the present invention, the method for determining an insulin dosing recommendation comprises: taking a measurement of blood glucose concentration in a patient at each of a plurality of actuation times; applying an adaptive filter scheme at each actuation time to generate an estimate of the patient's present physiological state based on the most recent measurement of blood glucose concentration; storing the estimate of the patient's present physiological state; and using Linear Quadratic methodology to determine an insulin dosing recommendation based on the estimate of the patient's present physiological state and based on any stored estimates of the patient's physiological state. It is also Particularly preferred that the actuation times are spaced at regular intervals of less than 15 minutes. More preferably at regular intervals of less than 10 minutes, at regular intervals of less than 5 minutes, or at regular intervals of less than 1 minute. Most preferably, the actuation times occur continuously, and the measurements of blood glucose concentration are processed in real-time.

The present invention also relates to an artificial pancreas control system comprising an observer, and an LQ Regulator. The observer preferably comprises a programmable computer controller, which is programmed to receive real-time measurements of blood glucose concentration in a patient, and to apply an adaptive filter scheme to estimate a present physiological state of a patient based on the measurements of blood glucose concentration. The LQ Regulator preferably comprises a programmable computer controller, which is programmed to receive the present physiological state estimation from the observer, to use Linear Quadratic methodology to determine an insulin dosing recommendation based on the present physiological state.

In preferred versions of the artificial pancreas control system according to the present invention, the LQ Regulator comprises a programmable computer controller programmed to present the insulin doing recommendation to the patient in an open-loop application, or directly to an insulin pump in a closed-loop application.

BRIEF DESCRIPTION OF THE DRAWINGS

These and other features, aspects, and advantages of the present invention will become better understood with reference to the following description and appended claims, and accompanying drawings where:

DETAILED DESCRIPTION OF THE INVENTION

The present invention may be understood more readily by reference to the following detailed description of preferred embodiments of the invention as well as to the examples included therein.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

In LQG control, an actuation signal is computed to minimize squared-error deviations from a nominal operating point, which in this case corresponds to tight glycemic control around a reference glucose concentration of 100 mg/dl. The feedback control law is derived from a linearized model of the system dynamics, which is assumed to be perturbed by Gaussian white noise disturbances and measurement errors. Then using the so-called separation principle of LQG, feedback control laws can be computed easily as a linear combination of least-squares estimates of the states of the system through feedback gains designed to minimize the integral of weighted squared errors and control signals in a noise-free system (i.e. LQR feedback gains).

The methods and Artificial Pancreas Control Systems according to the present invention can be used in a wide range of applications, described in detail below, but arise from a common general mechanism described in FIG. 1.

Figure 1:
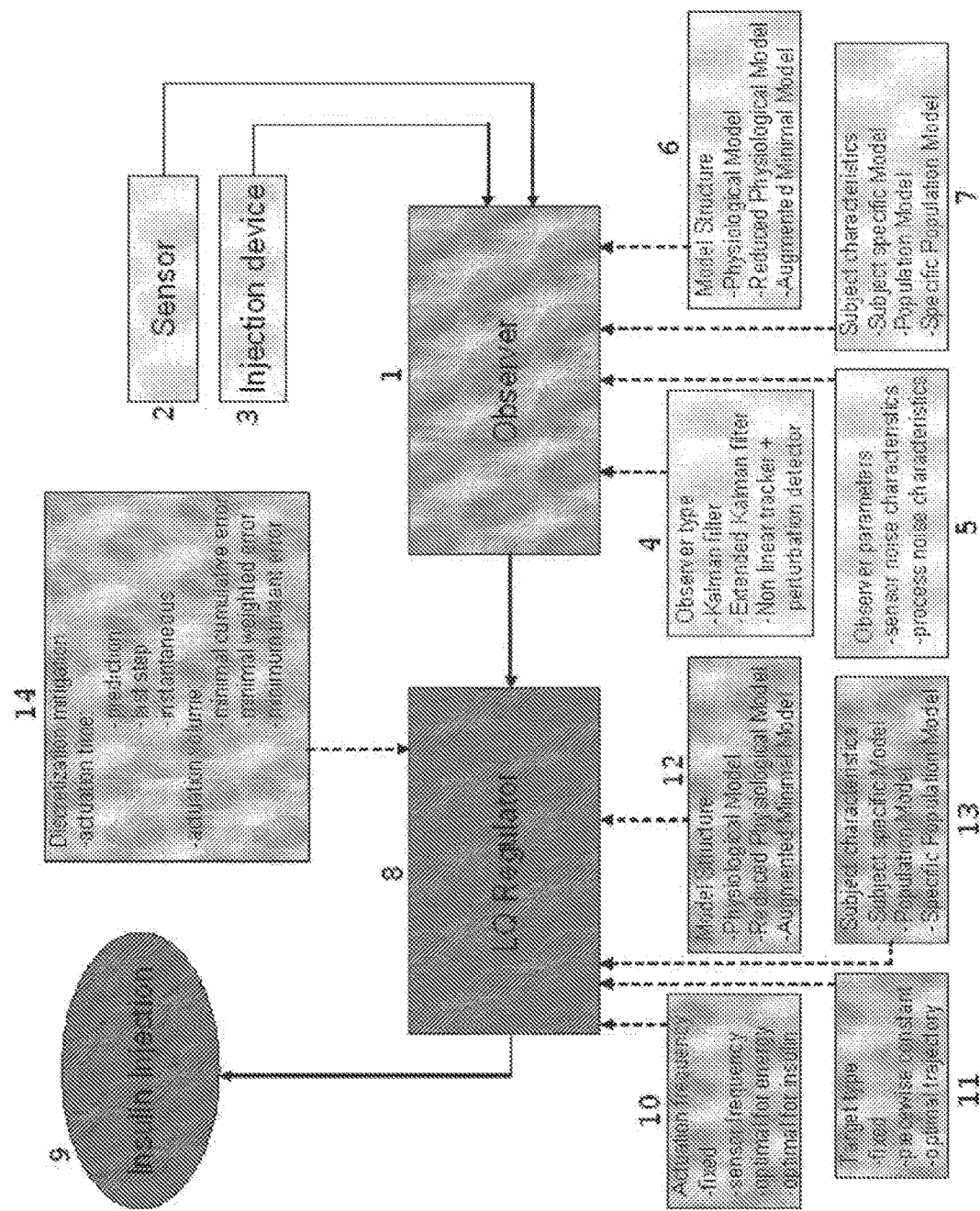
FIG. 1: shows a general schematic of the LQG based plasma glucose regulator.

As shown in FIG. 1, observer (1) receives information from sensor (2) and/or from injection device (3). This information can include, for example, a measurement of blood glucose concentration in a patient. Observer (1) then models the present physiological state of the patient. The modeled physiological state depends on the observer type (4), the observer parameters (5), the model structure (6), and the subject characteristics (7). The estimated physiological state is then applied to a Linear Quadratic (LQ) regulator (8). The LQ regulator (8) determines an insulin dosing recommendation, which is preferably used to determine an appropriate insulin injection (9). The determination of the insulin dosing recommendation depends on the actuation frequency (10), the target type (11), the model structure (12), the subject characteristics (13), and the discretization mitigation (14).

According to preferred versions of the present invention, blood glucose is measured frequently (<15 min), and these measures and information about insulin treatment are provided to a state observer. The state observer estimates the physiological state of the subject (different models impose different 'physiological states', including plasma glucose and insulin concentrations), while the Linear Quadratic regulator uses present and past estimations of the state to compute the needed insulin treatment.

While some characteristics of the methods and Artificial Pancreas Control Systems of the present invention are highly application specific (e.g. target type, or injection device feedback) the bulk of the method remains the same across application fields. In this section we present these general components.

Preferably at each received glucose measure (from the continuous sensor) the system updates its estimation of the physiological state of the subject, i.e. it's estimation of glucose concentration (not necessarily equal to the measure considering sensor errors) and insulin concentration (estimated from known injection and glucose measures). To perform this task, it is preferable to apply adaptive filter methodology, representing the subject state by a dynamic system (equation 1.1), where X is the physiological state and Y the outcome measure: in this case blood glucose concentration.

$$\begin{cases} \dot{X}(t) = A_t X(t) + B_t u(t) \\ Y(t) = C_t X(t) + D_t u(t) \end{cases} \quad (1.1)$$

From this formalism we derive the adaptive filter scheme given by equation 1.2 where X is the estimated state of the system.

$$\dot{\hat{X}}(t) = A_t \hat{X}(t) + B_t u(t) - L_t(Y(t) - C_t \hat{X}(t) - D_t u(t)) \quad (1.2)$$

The methodology for selection of the state vector (X), as well as the dynamic equation parameters (A, B, C D), and the innovation gain (L) is presented below.

Preferably, the choice of the state vector is made via two antagonistic criteria: the higher the dimension of the model (i.e. the number of modeled quantities: e.g. plasma glucose, plasma insulin, remote insulin) the more precisely the model can describe observed dynamics, and as such estimate the modeled quantities; but high dimensions also render the estimation procedure sensitive to noise in the observed signal (BG), lowering the precision of the state estimate, and can preclude the use of subject specific regulation (see below), due to unobservable states and non identifiable parameters. Preferred versions of the present invention, therefore utilize one of three dynamic models, with increasing dimensionality. All three models are original, though at their core lie published differential equations. The models, presented below, require increasingly difficult parameters estimation; however, selection of a dynamic model preferably depends on the need of the user.

The first model is augmented Minimal Model of Glucose Kinetics (AMMGK). Presented for the first time in 1979 (See, R N Bergman, Y Z Ider, CR Bowden, and C Cobelli. Quantitative estimation of insulin sensitivity. Am J Physio, 236:E667-EE677, 1979) the Minimal Model of Glucose Kinetics (MMGK) has since become the most used and well-known model of glucose homeostasis in humans. Its simplicity (the original model has 2 states) has allowed the introduction of key concepts like insulin sensitivity and remote insulin.

Preferred versions of the present invention employ augmented MMGK to take into account the transport of insulin from the injection site to the central circulation, and the transport of glucose from the stomach to the central circulation. The model is presented in equation (1.3), differential equations 1 and 3 are directly taken from the common form of the MMGK, and insulin kinetics are added in line 4. Since preferred versions of the present invention measure glucose subcutaneously, it is preferable to add a simple diffusion equation (line 2) to represent the transport of glucose from the compartment of interest (plasma) to the measuring site (interstitium). Lines 5 and 6 model the subcutaneous insulin transport after injection (J), while line 7 models the glucose rate of appearance from a meal (D). This model leads to a state vector of dimension 7, as shown in equation (1.3).

$$\begin{cases} \dot{G} = -S_g(G - G_b) - XG + \dfrac{Ra(t)}{V_g} \\ \dot{G}_i = -\dfrac{1}{\tau}(G_i - G) \\ \dot{X} = -p_2 X + p_3(I_p - I_{p_{basal}}) \\ \dot{I} = -nI + \dfrac{k_{a1} I_{SQ1} + k_{a2} I_{SQ2}}{V_i} \\ \dot{I}_{SQ1} = -(k_{a1} + k_d) I_{SQ1} + J(t) \\ \dot{I}_{SQ2} = -k_{a2} I_{SQ2} + k_d I_{SQ2} \\ \dot{Ra} = -\dfrac{1}{\tau_{meal}}(Ra - D(t)) \end{cases} \quad (1.3)$$

The second model is the reduced Meal Model (RMM). (Dalla Man et al. presented in 2007 a much more complicated model to represent glucose and insulin fluxes during a meal (C. Dalla Man, R. A. Rizza, and C. Cobelli. Meal simulation model of the glucose-insulin system. IEEE Trans Biomed Eng, in press 2007.) Using triple tracers, each flux was separately identified in more than 200 subjects and modeled via the simplest available equations.

Preferred versions of the present invention make use of this model by augmenting it in much the same way as the MMGK, using two subcutaneous insulin equations, an interstitial glucose equation and modeling the meal via a single equation. This departs from the initial model, which included a strongly non linear modeling of the rate of appearance of glucose, see next paragraph. The final result is a dynamic system of dimension 11, as shown in equation (1.4.)

$$\begin{cases} \dot{G}_p = -(k_2 + kp_2) G_p + k_1 G_t - U_{ii} - kp_3 I_d + Ra(t) + kp_1 \\ \dot{G}_t = -k_1 G_t + k_1 G_p - \dfrac{Vm_0 + Vm_X X}{Km_0 + G_t} G_t \\ \dot{G}_i = -\dfrac{1}{\tau_{IG}}\left(G_i - \dfrac{G_p}{V_g}\right) \\ \dot{I}_d = -k_i(I_d - I_1) \\ \dot{I}_1 = -k_i\left(I_1 - \dfrac{I_p}{V_i}\right) \\ \dot{I}_p = -(m_2 + m_4) I_p + m_1 I_l + k_{a1} I_{SQ1} + k_{a2} I_{SQ2} \\ \dot{I}_l = -(m_1 + m_3) I_p + m_2 I_p \\ \dot{X} = -p_{2u}\left(X - \dfrac{I_p}{V_i} + I_b\right) \\ \dot{I}_{SQ1} = -(k_{a1} + k_d) I_{SQ1} + J(t) \\ \dot{I}_{SQ2} = -k_{a2} I_{SQ2} + k_d I_{SQ2} \\ \dot{Ra} = -\dfrac{1}{\tau_{meal}}(Ra - D(t)) \end{cases} \quad (1.4)$$

The third model is the Augmented Meal Model (AMM). The model presented below is an extension of the model presented by Dalla Man, like the original it includes the non linear gastro-intestinal model (3 states), the 2 glucose compartments and the 5 insulin related states. However, according to preferred versions of the present invention the model is augmented by 2 additional insulin states for transport and an additional glucose compartment (interstitium). The resulting state, utilized in preferred versions of the present invention, is of dimension 13, as shown in equation (1.5).

$$\begin{cases} \dot{G}_p = -(k_2 + kp_2) G_p + k_1 G_t - U_{ii} - E(G_p) - kp_3 I_d + \dfrac{f k_{abs} Q_{gut}}{BW} + kp_1 \\ \dot{G}_t = -k_1 G_t + k_2 G_p - \dfrac{Vm_0 Vm_X X}{Km_0 + G_t} G_t \\ \dot{G}_i = -\dfrac{1}{\tau_{IG}}\left(G_i - \dfrac{G_p}{V_g}\right) \\ \dot{I}_d = -k_i(I_d - I_1) \\ \dot{I}_1 = -k_i\left(I_1 - \dfrac{I_p}{V_i}\right) \\ \dot{I}_p = -(m_2 + m_4) I_p + m_1 I_l + k_{a1} I_{SQ1} + k_{a2} I_{SQ2} \\ \dot{I}_l = -(m_1 + m_3) I_p + m_2 I_p \\ \dot{X} = -p_{2u}\left(X - \dfrac{I_p}{V_i} + I_b\right) \\ \dot{I}_{SQ1} = -(k_{a1} + k_d) I_{SQ1} + J(t) \\ \dot{I}_{SQ2} = -k_{a2} I_{SQ2} + k_d I_{SQ2} \\ \dot{Q}_{sto1} = -k_{gri} Q_{sto1} + D(t) \\ \dot{Q}_{sto2} = -k_{empt}(Q_{sto1} + Q_{sto2}) Q_{sto2} + k_{gri} Q_{sto1} \\ \dot{Q}_{gut} = -k_{abs} Q_{gut} + k_{empt}(Q_{sto1} + Q_{sto2}) Q_{sto2} \end{cases} \quad (1.5)$$

Where $E(G_p) = \begin{cases} ke_1(G_p - ke_2) & \text{if } G_p > ke_2 \\ 0 & \text{otherwise} \end{cases}$ and $k_{empt}(Q_{sto1} + Q_{sto2}) = k_{min} + \dfrac{k_{max} - k_{min}}{2}(2 + \tanh(aa(Q_{sto1} + Q_{sto2} - b\,\text{dose})) + \tanh(cc(Q_{sto1} + Q_{sto2} - d\,\text{dose})))$ $aa = \dfrac{2.5\,\text{dose}}{1 - b} \quad cc = \dfrac{2.5\,\text{dose}}{d}$ The state estimation filter presented in equation (1.2) relies on parameters of different nature to be usable: first the matrices $A_f$, $B_f$, $C_f$, and $D_f$ are derived using the chosen model (see above), the type of fit to the subject, the insulin used and the optimization procedure (see below). Then, depending on the characteristics of the process noise and the sensor noise, the optimization technique is used to compute the filter gain $L_f$. In the next paragraphs we describe in detail how to select preferable parameters in different scenarios.

As subjects can be widely different from one another, it is preferable, in order to observe a state vector, to tailor the used model to a particular subject. As preferred versions of the present invention employ 'physiological' models, some parameters are readily available, e.g. body weight (BW). However, most parameters are highly model specific and require some data collection before the regulator can be put online. In the following section we describe three preferred choices for the model parameters estimation, ranging from a fixed parameters, plug 'n play type, methodology to a fully subject specific observer.

According to preferred versions of the present invention, parameters can be fixed at population values. Each model has been fitted to enough subjects to derive averages of the parameters. Using the averages of the population, it is preferable to construct a model that is subject independent, and therefore does not require any tuning before use. Particularly preferred values of the parameters are reported below:

AMMGK: Sg=0.0094; Vg=2.5; p2=0.0265; p3=6.724e-6; Gh=142; n=0.2; Vi=0.125; m2=0.3616; m3=0.306; m4=0.1446; ka1=0.002; ka2=0.0211; kd=0.0166; p2u=0.0276; tauIG=0.2; Ib=104; tauMEAL=0.055;

RMM: Vg=1.834; k1=0.0702; k2=0.1151; kp2=0.0061; Uii=1; kp3=0.0087; kp1=5.1207; Vm0=5.3263; Vmx=0.0417; Km0=234.0043; ki=0.0075; Vi=0.0503; m2=0.3616; m3=0.306; m4=0.1446; ka1=0.002; ka2=0.0211; kd=0.0166; p2u=0.0276; tauIG=0.2; Ib=104;

AMM: Vg=1.834; k1=0.0702; k2=0.1151; kp2=0.0061; Uii=1; kp3=0.0087; kp1=5.1207; Vm0=5.3263; Vmx=0.0417; Km0=234.0043; ki=0.0075; Vi=0.0503; m2=0.3616; m3=0.306; m4=0.1446; ka1=0.002; ka2=0.0211; kd=0.0166; p2u=0.0276; kabs=0.2386; kmax=0.0384; kmin=0.0089; b=0.7705; f=0.9; d=0.1714; ke1=0.0005; ke2=339; tauIG=0.2; Ib=104; dose=90;

Mitigated population parameters for pump users: While population parameters are easy to use they suffer from a major drawback: at rest (steady state) there exists a bias between the estimated and the actual plasma glucose concentration, therefore making any regulator biased as well. To ensure the absence of bias while avoiding the full model fit it is particularly preferable to employ a methodology based on a single blood draw:

For AMM and RMM, a preferred procedure is as follows: (1) Draw blood (quantity depending on the assay used) after a minimum of 4 hours fasting and without insulin bolus or changes in insulin basal rate. Measure blood glucose concentration [mg/dl] and blood insulin concentration [pmol/L]. Record basal rate [mU/min]. (2) Modify the population parameters as follows: Vi=2.7648*basal_rate/Iss; Vg=349.5685/Gss. This modification cancels the bias by adjusting the diffusion volumes so that the population steady state quantities, which result from the population parameters and therefore are constant in this case (Ipss=2.7648*basal_rate pmol·kg$^{-1}$; Gpss=349.5685 mg·kg$^{-1}$) correspond to the measured concentration (Iss and Gss).

For AMMGK, it is preferable to follow the same procedure as before, replacing Ib and Gb respectively by Iss and Gss, and replacing Vi by 5*basal_rate/Iss.

To achieve a fully subject specific model particularly preferred versions of the present invention estimate most of the model parameters. Such estimations allow the estimator not only to be bias free at steady state, like the previous method, but to also capture all the dynamics of the system, allowing for a bias free estimation both in transient mode (when glucose is not stabilized at a constant value, which is most of the time) and steady state. This estimation is relatively easy for the AMMGK, more cumbersome for the RMM, and extremely difficult for the full MM.

Preferred versions of the present invention are based on analysis of an OGTT or IVGTT, which can be performed in a doctor's office. (1) The subject presents himself/herself after fasting for 8 hours having not changed the insulin basal_rate for 2 hours. (2) 0.5 g/kg$^{-1}$ of body weight of glucose is ingested (OGTT) or injected intravenously (IVGTT). (3) Inject (subcutaneously) x unit of insulin, x being calculated as per the patient carbohydrate ratio. (4) Venous blood is drawn and plasma glucose and insulin concentration are measured at minutes 0 5 10 30 45 60 90 120. (5) Using the driving function methodology, and the weighted least square criterion adjust the model parameters: the parameters are found to minimize the weighted sum of square of the difference between model and measure at each sampling point. Some parameters are estimated using the insulin measures, others the glucose. It is not advised to estimate all the parameters in one run.

Insulin characteristics: In all three models the transport of insulin from interstitium to central circulation is preferably modeled via 2 differential equations depending on 3 parameters. These 3 parameters depend of course on the subject but can also change with different type of insulin or mixtures thereof.

Versions of the present invention utilize fixed parameters. In these versions, all insulin are considered have the same dynamics, coarsely, and ka1, ka2 and kd are set to population values, or subject specific values depending on method chose.

Preferred versions of the present invention employ insulin specific parameters. In these versions, based on response curve provided by the industry, each insulin types is fit with a specific set of parameters, using the driving function methodology described above.

Preferred versions of the present invention employ optimal innovation gain selection. It is to be noted that while the proposed models are non linear, the estimator and the dynamic model it is based on are linear state space equations. Therefore, preferred versions of the present invention not only to determine an optimal gain (L), but also determine the matrices $A_f$, $B_f$, $C_f$, and $D_f$. In the next paragraphs we present two preferred optimization methods: the Kalman filter and the extended kalman filter.

Kalman filter optimization: In the Kalman methodology the state equation matrices (A, B, C, and D) are constant and correspond to the linearization of the physiological model around a specified operation point. The operation point should be chosen as the steady state target of the regulator, or if not available (control between bounds) as the expected average of the state.

Linearization is done as follows:

AMMGK:

$$\zeta_{op} = \begin{bmatrix} G_{target} \\ G_{target} \\ S_g \dfrac{G_{target} - G_b}{G_{target}} \\ \dfrac{p_2(G_{target} - G)_b + I_b}{p_3 G_{target}} \\ \dfrac{\left(\dfrac{S_g p_2(G_{target} - G)_b + I_b}{p_3 G_{target}}\right)}{(k_{a1} + k_d)nV_i} \\ \dfrac{k_d\left(\dfrac{S_g p_2(G_{target} - G)_b + I_b}{p_3 G_{target}}\right)}{k_{a2}(k_{a1} + k_d)nV_i} \\ 0 \end{bmatrix}$$

$$A = \begin{bmatrix} -S_g - X_{op} & 0 & G_{op} & 0 & 0 & 0 & \dfrac{1}{V_g} \\ \dfrac{1}{\tau} & -\dfrac{1}{\tau} & 0 & 0 & 0 & 0 & 0 \\ \dfrac{1}{\tau} & 0 & -p_2 & p_3 & 0 & 0 & 0 \\ 0 & 0 & 0 & -n & \dfrac{k_{a1}}{V_i} & \dfrac{k_{a2}}{V_i} & 0 \\ 0 & 0 & 0 & 0 & -(k_{a1}+k_d) & 0 & 0 \\ 0 & 0 & 0 & 0 & k_d & -k_{a2} & 0 \\ 0 & 0 & 0 & 0 & 0 & 0 & -\dfrac{1}{\tau_{meal}} \end{bmatrix}$$

$$B = \begin{bmatrix} 0 \\ 0 \\ 0 \\ 0 \\ 1 \\ 0 \\ 0 \end{bmatrix} \quad G = \begin{bmatrix} 0 \\ 0 \\ 0 \\ 0 \\ 0 \\ 0 \\ \dfrac{1}{\tau_{meal}} \end{bmatrix} \quad C = \begin{bmatrix} 0 \\ 1 \\ 0 \\ 0 \\ 0 \\ 0 \\ 0 \end{bmatrix} \quad D = \begin{bmatrix} 0 \\ 0 \\ 0 \\ 0 \\ 0 \\ 0 \\ 0 \end{bmatrix}$$

(1.6)

RMM:

$$\zeta_{op} = \begin{bmatrix} G_{pop} = V_g G_{target} \\ G_{top} = \dfrac{-\beta \pm \sqrt{B^2 - 4\alpha\gamma}}{2\alpha} \\ G_{target} \\ I_{dop} = \dfrac{-(k_1 + k_2)G_{pop} + k_2 G_{top} + kp1 - U_{ii}}{kp_3} \\ I_{lop} = I_{dop} \\ I_{pop} = \dfrac{I_{dop}}{V_i} \\ I_{kop} = \dfrac{m_2 I_{pop}}{m_1 + m_3} \\ X_{op} = I_{dop} - I_b \\ I_{sg1op} = \dfrac{(m_2 + m_4)I_{pop} - m_1 I_{lop}}{k_{a1} + k_d} \\ I_{sg2op} = \dfrac{k_d I_{sg1op}}{k_{a2}} \\ 0 \end{bmatrix}$$

where $\beta = k_1 G_{pop} - k_2 Km_0 - Vm_0 + Vm_X I_b - \dfrac{Vm_X(k_1 + kp_2)G_{pop} - Vm_X kp_1 + Vm_X U_{ii}}{kp3}$ $\alpha = -k_2 - \dfrac{Vm_X * k_2}{kp_3}$ $\gamma = k_1 G_{pop} Km_0$ $$B = \begin{bmatrix} 0 \\ 0 \\ 0 \\ 0 \\ 0 \\ 0 \\ 0 \\ 1 \\ 0 \\ 0 \end{bmatrix} \quad G = \begin{bmatrix} 0 \\ 0 \\ 0 \\ 0 \\ 0 \\ 0 \\ 0 \\ 0 \\ 0 \\ \dfrac{1}{\tau_{meal}} \end{bmatrix}$$

(1.7)

-continued $$A = \begin{bmatrix} -(k_1+kp_2) & \frac{k_2}{(Km_0+G_{top})^2} & 0 & -kp_3 & 0 & 0 & 0 & 0 & -\frac{Vm_X G_{top}}{Km_0+G_{top}} & 0 & 0 & 1 \\ k_1 & -k2 - \frac{(Vm_0+Vm_X X_{op})Km_0}{(Km_0+G_{top})^2} & 0 & 0 & 0 & 0 & 0 & 0 & 0 & 0 & 0 & 0 \\ \frac{1}{\tau_{IG}V_g} & 0 & -\frac{1}{\tau_{IG}} & 0 & 0 & 0 & 0 & 0 & 0 & 0 & 0 & 0 \\ 0 & 0 & 0 & -k_i & k_i & 0 & 0 & 0 & 0 & 0 & 0 & 0 \\ 0 & 0 & 0 & 0 & -k_i & \frac{k_i}{V_i} & 0 & 0 & 0 & 0 & 0 & 0 \\ 0 & 0 & 0 & 0 & 0 & -(m_2+n_4) & m_1 & 0 & 0 & 0 & 0 & 0 \\ 0 & 0 & 0 & 0 & 0 & m2 & -(m_1+m_3) & 0 & k_{a1} & k_{a2} & 0 & 0 \\ 0 & 0 & 0 & 0 & 0 & \frac{p_{2u}}{V_i} & 0 & -p_{2u} & 0 & 0 & 0 & 0 \\ 0 & 0 & 0 & 0 & 0 & 0 & 0 & 0 & -(k_{a1}+k_d) & 0 & 0 & 0 \\ 0 & 0 & 0 & 0 & 0 & 0 & 0 & 0 & k_d & -(k_d+k_d) & 0 & 0 \\ 0 & 0 & 0 & 0 & 0 & 0 & 0 & 0 & 0 & k_d & -k_{a2} & 0 \\ 0 & 0 & 0 & 0 & 0 & 0 & 0 & 0 & 0 & 0 & 0 & \frac{1}{\tau_{meal}} \end{bmatrix}$$

$$B = \begin{bmatrix} 0 & 0 & 0 & 0 & 0 & 0 & 0 & 0 & 0 & 0 & 0 & 0 \\ 0 & 0 & 0 & 0 & 1 & 0 & 0 & 0 & 0 & 0 & 0 & 0 \end{bmatrix}^T \quad G = \begin{bmatrix} 0 & 0 & 0 & 0 & 0 & 0 & 0 & 0 & 0 & 1 & 0 & 0 \end{bmatrix}^T$$

$$C = \begin{bmatrix} 0 & 0 & 1 & 0 & 0 & 0 & 0 & 0 & 0 & 0 & 0 & 0 \\ 0 & 0 & 0 & 0 & 0 & 0 & 0 & 0 & 0 & 0 & 0 & 1 \end{bmatrix} \quad D = \begin{bmatrix} 0 & 0 & 0 & 0 & 0 & 0 & 0 & 0 & 0 & 0 \\ 0 & 0 & 0 & 0 & 0 & 0 & 0 & 0 & 0 & 0 \end{bmatrix}$$

(1.8)

AMM:

$$\zeta_{op} = \begin{bmatrix} G_{pop} = V_g G_{target} \\ G_{top} = \frac{-\beta \pm \sqrt{B^2 - 4\alpha\gamma}}{2\alpha} \\ G_{target} \\ I_{dop} = \frac{-(k_1+k_2)G_{pop}+k_2 G_{top}+kp1-Uii}{kp_3} \\ I_{top} = I_{dop} \\ I_{pop} = \frac{I_{dop}}{V_i} \\ I_{kop} = \frac{m_2 I_{pop}}{m_1+m_3} \\ X_{op} = I_{dop} - I_b \\ I_{sq1op} = \frac{(m_2+m_4)I_{pop} - m_1 I_{op}}{k_{a1}+k_d} \\ I_{sq2op} = \frac{k_d I_{sq1op}}{k_{a2}} \\ 0 \\ 0 \\ 0 \\ 0 \end{bmatrix}$$

where $\beta = k_1 G_{pop} - k_2 Km_0 Vm_0 + Vm_X I_b + \frac{Vm_X(k_1+kp_2)G_{pop} - Vm_X kp_1 + Vm_X U_{ii}}{kp_3}$ $\alpha = -k_2 - \frac{Vm_X k_2}{kp_3}$ $\gamma = k_1 G_{pop} Km_0$ -continued $$A = \begin{bmatrix} -(k_1+kp_2) & k_2 & 0 & -kp_3 & 0 & 0 & 0 & 0 & 0 & 0 & 0 & 0 & 0 \\ k_1 & -k2 - \frac{(Vm_0+Vm_X X_{op})Km_0}{(Km_0+G_{op})^2} & 0 & 0 & 0 & 0 & -\frac{Vm_X G_{top}}{Km0+G_{top}} & 0 & 0 & 0 & 0 & 0 & 0 \\ \frac{1}{\tau_{IG} V_g} & 0 & -\frac{1}{\tau_{IG}} & 0 & 0 & 0 & 0 & 0 & 0 & 0 & 0 & 0 & 0 \\ 0 & 0 & 0 & -k_i & 0 & 0 & 0 & 0 & 0 & 0 & 0 & 0 & 0 \\ 0 & 0 & 0 & k_i & -k_i & 0 & 0 & 0 & 0 & 0 & 0 & 0 & 0 \\ 0 & 0 & 0 & -k_i & 0 & \frac{k_i}{V_i} & 0 & 0 & 0 & 0 & 0 & 0 & 0 \\ 0 & 0 & 0 & 0 & 0 & 0 & -(m_2+m_4) & m_1 & 0 & 0 & 0 & 0 & 0 \\ 0 & 0 & 0 & 0 & 0 & 0 & m_2 & -(m_1+m_3) & 0 & k_{a1} & k_{a2} & 0 & 0 \\ 0 & 0 & 0 & 0 & 0 & 0 & \frac{p_{2u}}{V_i} & 0 & -p_{2u} & 0 & 0 & 0 & 0 \\ 0 & 0 & 0 & 0 & 0 & 0 & 0 & 0 & 0 & -(k_{a1}+k_d) & 0 & 0 & 0 \\ 0 & 0 & 0 & 0 & 0 & 0 & 0 & 0 & 0 & k_d & -k_{a2} & 0 & 0 \\ 0 & 0 & 0 & 0 & 0 & 0 & 0 & 0 & 0 & 0 & 0 & -k_{gri} & 0 \\ 0 & 0 & 0 & 0 & 0 & 0 & 0 & 0 & 0 & 0 & 0 & k_{gri} & -k_{emptop} & 0 \\ 0 & 0 & 0 & 0 & 0 & 0 & 0 & 0 & 0 & 0 & 0 & 0 & k_{emptop} & -k_{abs} \end{bmatrix}$$

$$C = \begin{bmatrix} 0 & 0 & 1 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & \frac{fk_{abs}}{BW} \end{bmatrix} \quad D = \begin{bmatrix} 0 \\ 0 \end{bmatrix}$$

Where $k_{emptop} = -aa - \frac{k\max - k\min}{2}(2 - \tanh^2(aa.b.dose) - \tanh^2(cc.d.dose))$  $aa = \frac{2.5\,dose}{1-b}$  $cc = \frac{2.5\,dose}{d}$ Computation of $\hat{X}$: Using equations (1.1) and one of the three linear models above, it is preferable to form the system presented in equation (1.9). The initial equation is preferably modified to take into account the controlled aspect of the model, namely disturbances such as meals are left unknown (represented as $W_n$) while insulin injections are considered known ($U_n$). Also, noise is preferably added to the output ($V_n$) and the system is presented in its discrete form.

$$\xi_n = A\xi_{n-1} + BU_{n-1} + GW_{n-1},$$

$$Y_n = C\xi_n + V_n$$

Where $\xi = X - \xi_{op}$ \hfill (1.9)

Assuming W and V (process noise/measurement noise) have means 0 and covariance matrices K and R respectively, it is preferable to build the estimator as:

$$\text{time update (predict)} \begin{cases} \hat{\xi}_{n|n-1} = A\hat{\xi}_{n-1} + BU_{n-1} \\ P_n^{n-1} = AP_{n-1}A^T + Q \\ L_n = P_n^{n-1}C^T(CP_n^{n-1}C^T + R)^{-1} \end{cases} \quad (1.10)$$

$$\text{Measurement update (correct)} \begin{cases} \hat{\xi}_n = \hat{\xi}_{n|n-1} + L_n(Y_n - C\hat{\xi}_{n|n-1}) \\ P_n = (I - L_nC)P_n^{n-1} \end{cases}$$

The choices of K and R are important, and particularly preferred versions of the present invention use K=0.01, and R=1. $\hat{\xi}$ is our state estimate and P, is the estimation error covariance matrix. So, according to preferred versions of the present invention, we have:

$$\hat{X} = \hat{\xi} + \zeta_{op}, \quad P_n = E[(X-\hat{X})(X-\hat{X})^T]$$

Extended Kalman filter optimization: In the extended Kalman methodology the linearization is not done off-line but within the recursive filter: the EKE takes into account the non-linear nature of the system and linearizes for each iterations around the predicted state (see Kalman filter above), therefore creating A, B, C, and D matrices that change with time. Preferred versions of the present invention derive again the linearization as for the KF but this time we consider $\tilde{X}_{m|n-1}$ known, which will be consistent with the algorithm described below.

AMMGK:

$$\begin{bmatrix} G_{op} \\ G_{iop} \\ X_{op} \\ I_{op} \\ I_{SQ1op} \\ I_{SQ2op} \\ Ra_{op} \end{bmatrix} = \hat{x}_{n|n-1} \quad A = \begin{bmatrix} -S_g - X_{op} & 0 & G_{op} & 0 & 0 & 0 & 0 \\ \frac{1}{\tau} & -\frac{1}{\tau} & 0 & 0 & 0 & 0 & 0 \\ 0 & 0 & -p_2 & p_3 & 0 & 0 & 0 \\ 0 & 0 & 0 & -n & \frac{K_{a1}}{V_i} & \frac{K_{a2}}{V_i} & 0 \\ 0 & 0 & 0 & 0 & -(k_{a1}+k_d) & 0 & 0 \\ 0 & 0 & 0 & 0 & k_d & -k_{a2} & 0 \\ 0 & 0 & 0 & 0 & 0 & 0 & 0 \end{bmatrix} \quad B = \begin{bmatrix} 0 \\ 0 \\ 0 \\ 0 \\ 0 \\ 0 \\ 0 \end{bmatrix} \quad G = \begin{bmatrix} \frac{1}{V_g} & 0 \\ 0 & 0 \\ 0 & 0 \\ 0 & 0 \\ 0 & 0 \\ 0 & 0 \\ \frac{1}{\tau_{meal}} \end{bmatrix} \quad C = \begin{bmatrix} 0 & 1 & 0 & 0 & 0 & 0 & 0 \\ 0 & 0 & 0 & 0 & 0 & 0 & 1 \end{bmatrix} \quad D = \begin{bmatrix} 0 & 0 \\ 0 & 0 \end{bmatrix} \quad (1.11)$$

RMM:

$$\begin{bmatrix} G_{pop} \\ G_{top} \\ G_{iop} \\ G_{dop} \\ I_{dop} \\ I_{top} \\ I_{pop} \\ X_{op} \\ I_{sq1op} \\ I_{sq2op} \\ Ra_{op} \end{bmatrix} = \hat{x}_{n|n-1} \quad B = \begin{bmatrix} 0 \\ 0 \\ 0 \\ 0 \\ 0 \\ 0 \\ 0 \\ 0 \\ 0 \\ 0 \\ 0 \end{bmatrix} \quad G = \begin{bmatrix} 0 & 0 \\ 0 & 0 \\ 0 & 0 \\ 0 & 0 \\ 0 & 0 \\ 0 & 0 \\ 0 & 0 \\ 0 & 0 \\ 0 & 0 \\ 0 & 0 \\ 0 & \frac{1}{\tau_{meal}} \end{bmatrix} \quad C = \begin{bmatrix} 0 & 1 & 0 & 0 & 0 & 0 & 0 & 0 & 0 & 0 & 0 \\ 0 & 0 & 0 & 0 & 0 & 0 & 0 & 0 & 0 & 0 & 1 \end{bmatrix} \quad D = \begin{bmatrix} 0 & 0 \\ 0 & 0 \end{bmatrix} \quad (1.12)$$

AMM:

$$A = \begin{bmatrix} -(k_1+kp_2) & k_2 & 0 & -kp_3 & 0 & 0 & 0 & 0 & 0 & 0 & 0 \\ k_1 & -k2 - \frac{(Vm_0+Vm_X X_{op})Km_0}{(Km_0+G_{top})^2} & 0 & 0 & -k_i & 0 & 0 & \frac{Vm_X G_{top}}{Km_0+G_{top}} & 0 & 0 & 0 \\ \frac{1}{\tau_{IG}V_g} & 0 & -\frac{1}{\tau_{IG}} & 0 & 0 & 0 & 0 & 0 & 0 & 0 & 0 \\ 0 & 0 & 0 & 0 & k_i & -k_i & 0 & 0 & 0 & 0 & 0 \\ 0 & 0 & 0 & 0 & -(m_2+m_4) & m_2 & 0 & 0 & 0 & 0 & 0 \\ 0 & 0 & 0 & 0 & \frac{k_i}{V_i} & \frac{p_{2u}}{V_i} & -(m_1+m_3) & 0 & 0 & 0 & 0 \\ 0 & 0 & 0 & 0 & 0 & 0 & m_1 & k_{a1} & k_{a2} & 0 & 0 \\ 0 & 0 & 0 & 0 & 0 & -p_{2u} & 0 & -(k_{a1}+k_d) & 0 & -k_{a2} & 0 \\ 0 & 0 & 0 & 0 & 0 & 0 & 0 & k_d & 0 & 0 & 0 \\ 0 & 0 & 0 & 0 & 0 & 0 & 0 & 0 & 0 & 0 & -\frac{1}{\tau_{meal}} \end{bmatrix} \quad (1.13)$$

-continued $$\begin{bmatrix} G_{pop} \\ G_{top} \\ G_{iop} \\ I_{dop} \\ I_{Lop} \\ I_{pop} \\ I_{top} \\ X_{op} \\ I_{sq2op} \\ Q_{so1op} \\ Q_{so2op} \\ Q_{guiop} \end{bmatrix} = \hat{X}_{n|n-1} \quad B = \begin{bmatrix} 0 & 0 \\ 0 & 0 \\ 0 & 0 \\ 0 & 0 \\ 0 & 0 \\ 0 & 0 \\ 0 & 0 \\ 0 & 0 \\ 1 & 0 \\ 0 & 0 \\ 0 & 0 \\ 0 & 0 \end{bmatrix} \quad G = \begin{bmatrix} 0 & 0 & 0 & 0 \\ 0 & 0 & 0 & 0 \\ 0 & 0 & 0 & 0 \\ 0 & 0 & 1 & 0 \\ 0 & 0 & 0 & 0 \\ 0 & 0 & 0 & 0 \\ 1 & 0 & 0 & 0 \\ 0 & 0 & 0 & 0 \\ 0 & 0 & 0 & 0 \\ 0 & 1 & 0 & 0 \\ 0 & 0 & 0 & 0 \\ 0 & 0 & 0 & 0 \end{bmatrix} \quad C = \begin{bmatrix} 0 & 0 & 1 & 0 & 0 & 0 & 0 & 0 & 0 & 0 & 0 & 0 \end{bmatrix} \quad D = \begin{bmatrix} 0 & 0 \end{bmatrix}$$

$$A = \begin{bmatrix}
-(k_1 + kp_2) & 0 & -kp_3 & 0 & 0 & 0 & 0 & 0 & 0 & 0 & 0 & 0 \\
k_1 & -k2 - \frac{(Vm_0 + Vm_X X_{op})Km_0}{(Km_0 + G_{top})^2} & 0 & 0 & 0 & 0 & 0 & -\frac{Vm_X G_{top}}{Km_0 + G_{top}} & 0 & 0 & 0 & 0 \\
\frac{1}{\tau_{IG} V_g} & k_2 & -\frac{1}{\tau_{IG}} & 0 & 0 & 0 & 0 & 0 & 0 & 0 & 0 & 0 \\
0 & 0 & 0 & -k_i & k_i & 0 & 0 & 0 & 0 & 0 & 0 & 0 \\
0 & 0 & 0 & 0 & -k_i & \frac{k_i}{V_i} & 0 & 0 & 0 & 0 & 0 & 0 \\
0 & 0 & 0 & 0 & 0 & -(m_2+m_4) & m_1 & 0 & 0 & 0 & 0 & 0 \\
0 & 0 & 0 & 0 & 0 & m_2 & -(m_1+m_3) & 0 & 0 & 0 & 0 & 0 \\
0 & 0 & 0 & 0 & 0 & \frac{p_{2u}}{V_i} & 0 & -p_{2u} & 0 & 0 & 0 & 0 \\
0 & 0 & 0 & 0 & 0 & 0 & 0 & 0 & k_{a1} & 0 & 0 & 0 \\
0 & 0 & 0 & 0 & 0 & 0 & 0 & 0 & -(k_{a1}+k_d) & k_d & 0 & 0 \\
0 & 0 & 0 & 0 & 0 & 0 & 0 & 0 & 0 & -k_{a2} & 0 & 0 \\
0 & 0 & 0 & 0 & 0 & 0 & 0 & 0 & 0 & 0 & -k_{gri} & -(k_{emptop} + Q_{st2op} k_{emptop}^{(1)}) & \frac{fk_{abs}}{BW} \\
0 & 0 & 0 & 0 & 0 & 0 & 0 & 0 & 0 & 0 & k_{gri} & (k_{emptop} + Q_{st2op} k_{emptop}^{(1)}) & -k_{abs}
\end{bmatrix}$$

Where $k_{emptop} = k_{min} + \frac{k\max - k\min}{2} (2 + \tanh(aa(Q_{so1op} + Q_{so2op}) - b.dose)) + \tanh(cc(Q_{so1op} + Q_{so2op} - d.dose)))$ $k_{emptop}^{(1)} = \frac{k\max - k\min}{2} (2 - \tanh^2(aa(Q_{so1op} + Q_{so2op} - b.dose)) - cc\tanh(cc(Q_{so1op} + Q_{so2op} - d.dose)))$ $aa = \frac{2.5 \, dose}{1-b} \quad cc = \frac{2.5 \, dose}{d}$ Computation of $\hat{X}$: Using equations (1.1) and one of the three original models, it is preferable to form the system presented in equation (1.4).

$$X_n = f(X_{n-1}, U_{n-1}, W_{n-1})$$

$$Y = h(x_n, V_t) \quad (1.14)$$

Where f and h are two non-linear functions defined by the chosen model. Assuming W and V (process noise/measurement noise) have means 0 and covariance matrices K and R respectively. It is preferable to build the estimator as:

$$\text{time update (predict)} \begin{cases} \hat{X}_{n|n-1} = f(\hat{X}_{n-1}, U_{n-1}, 0) \\ P_n^{n-1} = A_n P_{n-1} A_n^T + G_n Q_{k-1} G_n^T \end{cases}$$

$$\text{Measurement update (correct)} \begin{cases} L_n = P_n^{n-1} C_n^T (C_n P_n^{n-1} C_n^T + R_n)^{-1} \\ \hat{X}_n = \hat{X}_{n|n-1} + L_n(Y_n - h(\hat{X}_{n|n-1}, 0)) \\ P_n = (I - L_n C_n) P_n^{n-1} \end{cases}$$

Where $A_n$, $G_n$, and $C_n$ are the linearized matrices

The choices of K and R are important, and particularly preferred versions of the present invention use K=0.01, and R=1.

LQ regulator: The second component that is common to all application fields is the regulator, which transforms our knowledge of the physiological state of the system (from last section) into an insulin dosing recommendation. The LQ regulator preferably performs three steps: (i) Step 1 receives a state estimation; (ii) Step 2 uses the state and a predefined gain to compute the insulin dose; (iii) Step 3 presents the insulin dose recommendation to the patient in open-loop application, or directly to the insulin pump in closed-loop application.

Acquiring the estimate of the state: The estimate is preferably acquired at each actuation time (depending of the chosen actuation frequency) by running the chosen observer from last actuation time, using the last state estimates and covariance matrix as initial values, to the current actuation time, taking into account all intermediate sensor measures.

Calculating the optimal insulin dose: To compute the insulin dose it is preferable to use the Linear Quadratic methodology: the insulin injection is preferably defined as a linear combination of a gain vector (S) and the state vector (X), so as to minimize a quadratic cost function.

Assuming the subject glucose and insulin dynamics can be modeled by equation (1.1), tailored using one of the linearization scheme (equations (1.6) to (1.13), preferred versions of the present invention construct the following cost function to be minimized:

$$J = \int X^T Q X + U^T R U \quad (1.15)$$

The LQR gain (S) minimizing J is the solution of the following Riccati equation:

$$Q \pm A^T S + SA - (SB \pm N) R^{-1} (B^T S \pm N^T) = 0 \quad (1.16)$$

Choosing Q and R: The choice of Q and R determines both the states that are of interest (glucose vs. insulin, plasma concentration vs. other compartment) and the aggressiveness of the regulator (how fast it will try to achieve the selected target, therefore risking to dip under). In a simulation analysis, it was found that only the ration of Q over R is critical, and therefore preferred versions of the invention fix R at 1.

The choice of Q can be achieved in different ways, which are presented in the following paragraph, but always depends on the reliability of the sensor, the frequency of actuation (therefore the value is application dependent), and the subject characteristics. While not all of this information is always available, it is important to note that Q needs to be tailored for every implementation of the regulator. Preferred versions of the invention use the following structure for the Q vector:

AMMGK: Q=[q q 1 1 1 1 1]

RMM: Q=[q q q 1 1 1 1 1 1 1]

AMM: Q=[q q q 1 1 1 1 1 1 1 1 1 1]

Fixed q.: In a 'one size fits all' approach, preferred versions of the present invention, use a single vector Q for all subjects. In these versions, it is therefore important to choose a Q vector that minimizes the risk of dip below the target while achieving reasonable control. The following methodology is preferably employed:

(1) Using a meal simulator (e.g. See, C Dalla Man, D M. Raimondo, R A. Rizza, C Cobelli: GIM, Simulation Software of Meal Glucose—Insulin Model, Journal of Diabetes Science and Technology, 1(3): Page 323-330, 2007) for 100 subjects simulate a 45 g carbohydrate meal using the chosen regulation strategy and q between 1 and 500.

(2) Record the time to target (t2tgt) defined as the number of minutes it takes each in-silico subject to come back within 10 mg/dl of the intended target.

(3) Record the time below target (tbtgt) defined as the number of minutes spent below 2 mg/dl of the intended target.

(4) Compute J(q) as:

$$J(q) = \frac{1}{100} \sum_{i=1}^{100} t2tgt(q)_i + tbtgt(q)_i \quad (1.17)$$

Figure 2:
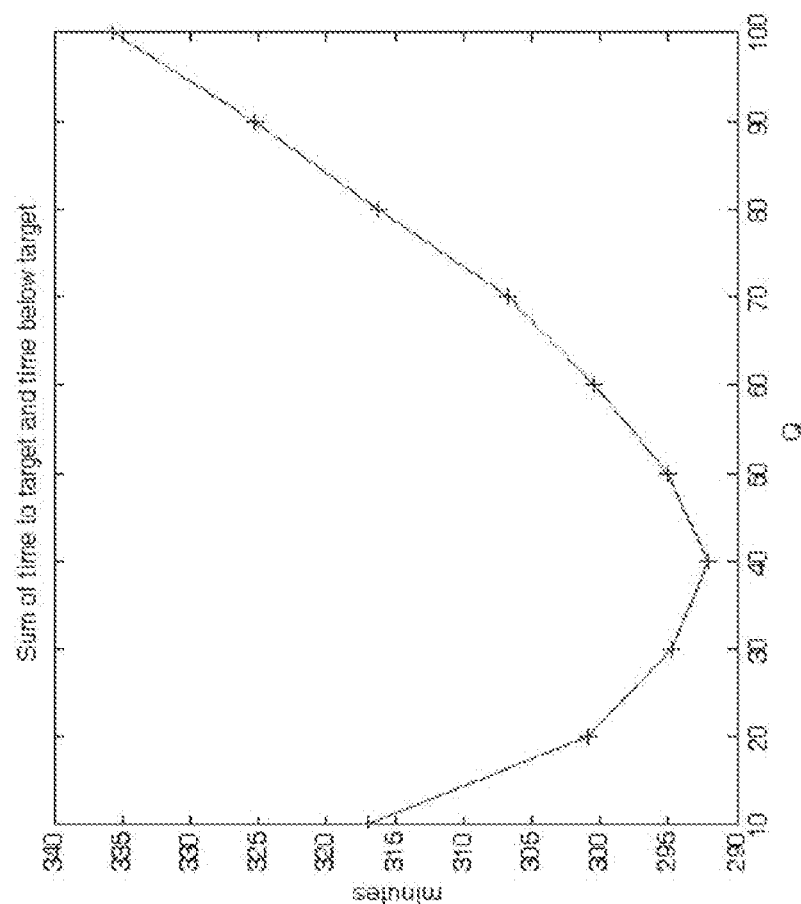
FIG. 2: shows a graph for choosing an optimal 'fit all' Q, i.e., finding the optimal LQ weight for a population, based on simulation and the time to target and time below target criteria.

(5) The optimal parameter Q* (see, FIG. 2) is defined as:

$$q^* = \underset{q}{\operatorname{argmin}} J(q) \quad (1.18)$$

Subject Specific q.: If the subject model parameters are known it is preferable to tailor the regulator to this particular subject, therefore improving dramatically the performances of the regulator. To estimate the optimal q parameter for a specific subject we propose the following method is preferably employed:

(1) Using a meal simulator (e.g. C Dalla Man, D M. Raimondo, R A. Rizza, C Cobelli: GIM, Simulation Software of Meal Glucose—Insulin Model, Journal of Diabetes Science and Technology, 1(3): Page 323-330, 2007) and the subject characteristics simulate a 45 g carbohydrate meal using the chosen regulation strategy and q equal 1, 250 and 500, respectively named $q_{min}$, $q_{mec}$, and $q_{max}$.

(2) For each q compute tbtgt as defined above.

(3) If tbtgt($q_{min}$)>0 restart step 1 with a lower $q_{min}$ value.

(4) If tbtgt ($q_{max}$)=0 restart step 1 with a higher $q_{max}$ value.

(5) simulate with $q=q_{med}$
  If tbtgt(q)=0
    $q_{min}=q_{mec}$
    $q_{med}=(q_{max}-q_{min})/2$
  else if tbtgt(q)>0
    $q_{max}=q_{mec}$
    $q_{med}=q_{max}-q_{min}/2$
(6) If $(q_{max}-q_{min})>1$ iterate step 3
(7) $q^*=q_{min}$ Target tracking method: According to preferred versions of the present invention, the LQ method is adapted to track an offline optimal trajectory. In these versions, the state equations around the target value at each actuation time are linearized by coupling a meal detection or meal announcement device and a meal trajectory (computed from past data or stored in the device). These versions then compute S as the solution of the new Riccati equation (since A, B, C, D and G have changed).

Figure 3:
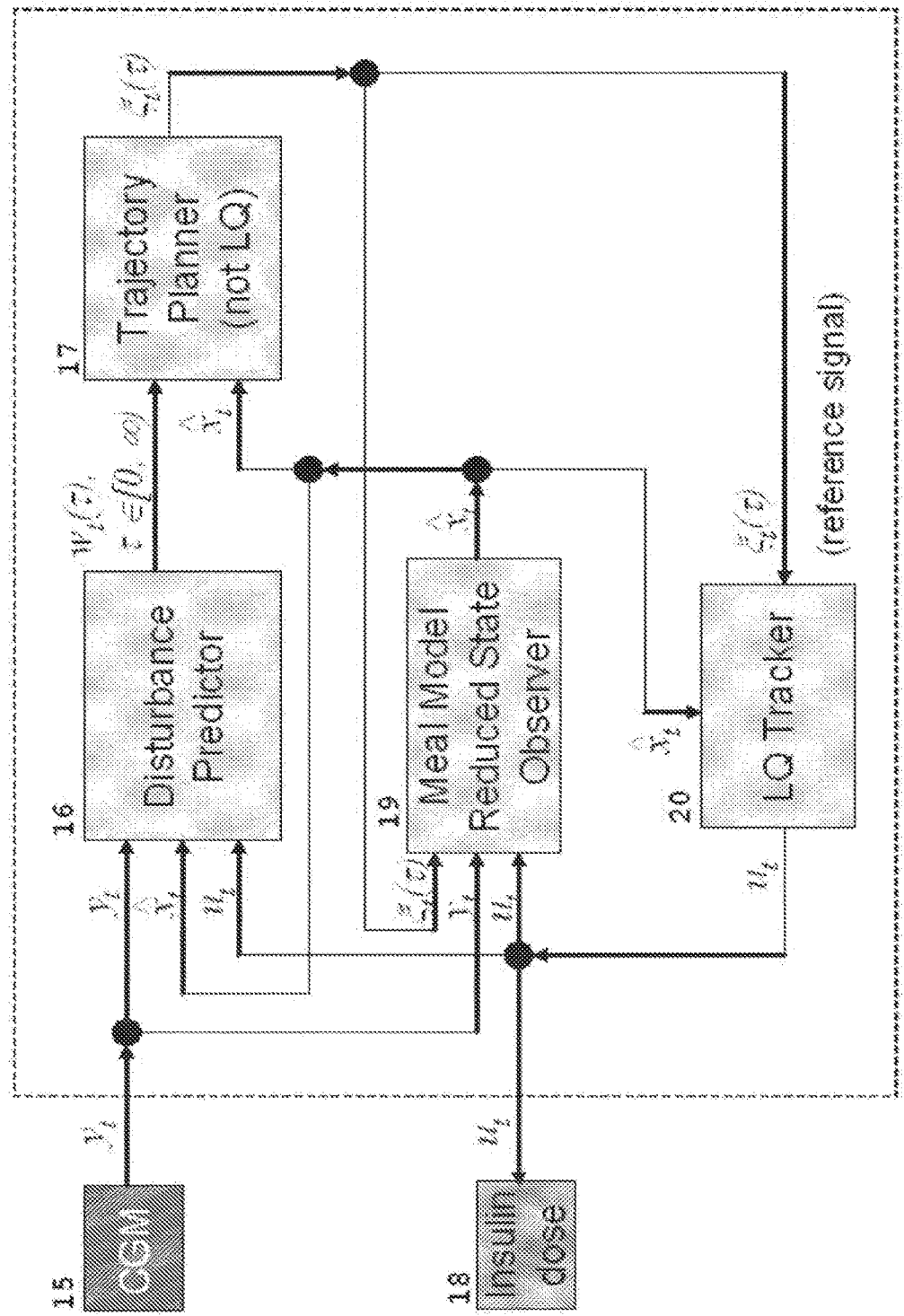
FIG. 3: shows a diagram of the target tracking extension of the LQ regulator.

FIG. 3 shows a target tracking Linear Quadratic (LQ) control system according to preferred versions of the present invention. As shown in FIG. 3, a meal model reduced state observer (19) is coupled with a disturbance predictor (16), a trajectory planner (17), and an LQ tracker (20) to track offline optimal trajectory based on Continuous Glucose Monitoring (CGM) (15). This system generates an insulin dosing recommendation, which is preferably used to determine an appropriate insulin dose (18).

Calculation of the injection: The LQR methodology assumes continuous or very frequent information about the insulin injection, which is not accessible in many implementations. To mitigate this discrepancy preferred versions of the present invention use three methods to compute the insulin injection, knowing the LQ parameters (linear model, Q, and R). For all the following methods it is assumed that the injection is continuous over the actuation period, in the case of non continuous actuation (like boluses) the method needs to be adapted by taking the final result (Inj) and multiplying by the actuation period $(t_n-t_{n-1})$ to obtain the total dose to be injected.

Instantaneous Injection: At each actuation decision time n (to be determined by the actuation frequency, based on application), it is preferable to compute the product of the LQ gain (S) by the estimated state vector (S).

$$Inj = X \cdot \hat{X}_n \quad (1.19)$$

Observed average injection: At each actuation decision time n, it is preferable to compute the average theoretical injection over the last actuation period (time since last actuation time n−1).

$$Inj = \frac{1}{t_n - t_{n-1}} \int_{t_{n-1}}^{t_n} S \cdot \hat{X}_t dt \quad (1.20)$$

Where $\hat{X}_t$ is equal to $\hat{X}_{t^*}$, and t* is the last time of a sensor reading such that $t^* \le t$.

Predicted average injection: At each actuation decision time n, it is preferable to compute the average theoretical injection over the next actuation period (time since last actuation time n−1). This means using the linearized system to predict the state over the injection period and computing the optimal injection over the period, then computing the average injection to use in Practice, see equation (1.21).

$$Inj = \frac{1}{t_{n+1} - t_n} \int_{t_n}^{t_{n+1}} S \cdot \tilde{X}_t dt \quad (1.21)$$

$$\dot{\tilde{X}}_t = A\tilde{X}_t + BU$$

$$\tilde{X}_{t_n} = \hat{X}_{t_n}$$

Tailoring the insulin injection to the injection device: To use a regulator properly we need to take into account the characteristics of the hardware, i.e. maximum and minimum injection rate for pumps, maximum and minimum amount for bolus injection devices, maximum and minimum update frequency for pumps, minimal increment in insulin dosing for both pump and bolus injection devices. Each limitation has influence on the theoretical injection calculated in the above section. Preferred versions of the present invention use several methods to mitigate these injection hardware shortcomings:

Minimal instantaneous error: In preferred versions of the present invention, the LQ optimal injection is rounded to the closest available value.

$$Inj_{final} = \text{round}[Inj/\text{increment}] \times \text{increment} \quad (1.22)$$

In the case of an insulin pump, preferred versions of the present invention achieve better error minimization by using the duration of injection. Considering an actuation period of T, and possible bolus durations of $d_1 \le \ldots < d_p < T$ we can construct the following injection:

$$Inj_{final} = \text{round}\left[\frac{Inj}{\text{increment} \times d_i}\right] \times \text{increment over } d_i \text{ minutes} \quad (1.23)$$

where $$i = \underset{j=1,\ldots,p}{\text{argmin}}\left(\left|Inj - \text{round}\left[\frac{Inj}{\text{increment} \times d_j}\right]\right| \times \text{increment} \times d_j\right)$$

Minimal cumulative error: In preferred versions of the present invention, the new injection is calculated as the injection optimizing the cumulative error (since beginning of operation) between LQ injection and actual injection:

$$Inj_{final}(t_n) = \text{round}\left[\frac{Inj_{t_n} + \varepsilon_{t_n}}{\text{increment}}\right] \times \text{increment} \quad (1.24)$$

$$\varepsilon_{t_n} = \varepsilon_{t_{n-1}} + Inj_{t_n} - Inj_{final}(t_n)$$

$$\varepsilon_{t_0} = Inj_{t_0} - Inj_{final}(t_0)$$

Minimal cumulative error with forgetting factor: In preferred versions of the present invention, the new injection is calculated as the injection optimizing the cumulative weighted error since beginning of operation) between LQ injection and actual injection, therefore old unresolved errors do not influence the decision.

$$Inj_{final}(t_n) = \text{round}\left[\frac{Inj_{t_n} + \varepsilon_{t_n}}{\text{increment}}\right] \times \text{increment} \quad (1.25)$$

$$\varepsilon_{t_n} = \sum_{i=1}^{n} e^{\gamma(t_i - t_n)}(Inj_{t_i} - Inj_{final}(t_i))$$

γ is the forgetting factor, the higher γ, the less past errors influence the new injection. Particularly preferred versions of the present invention use a value of $\gamma=0.07$ min$^{-1}$.

Figure 4:
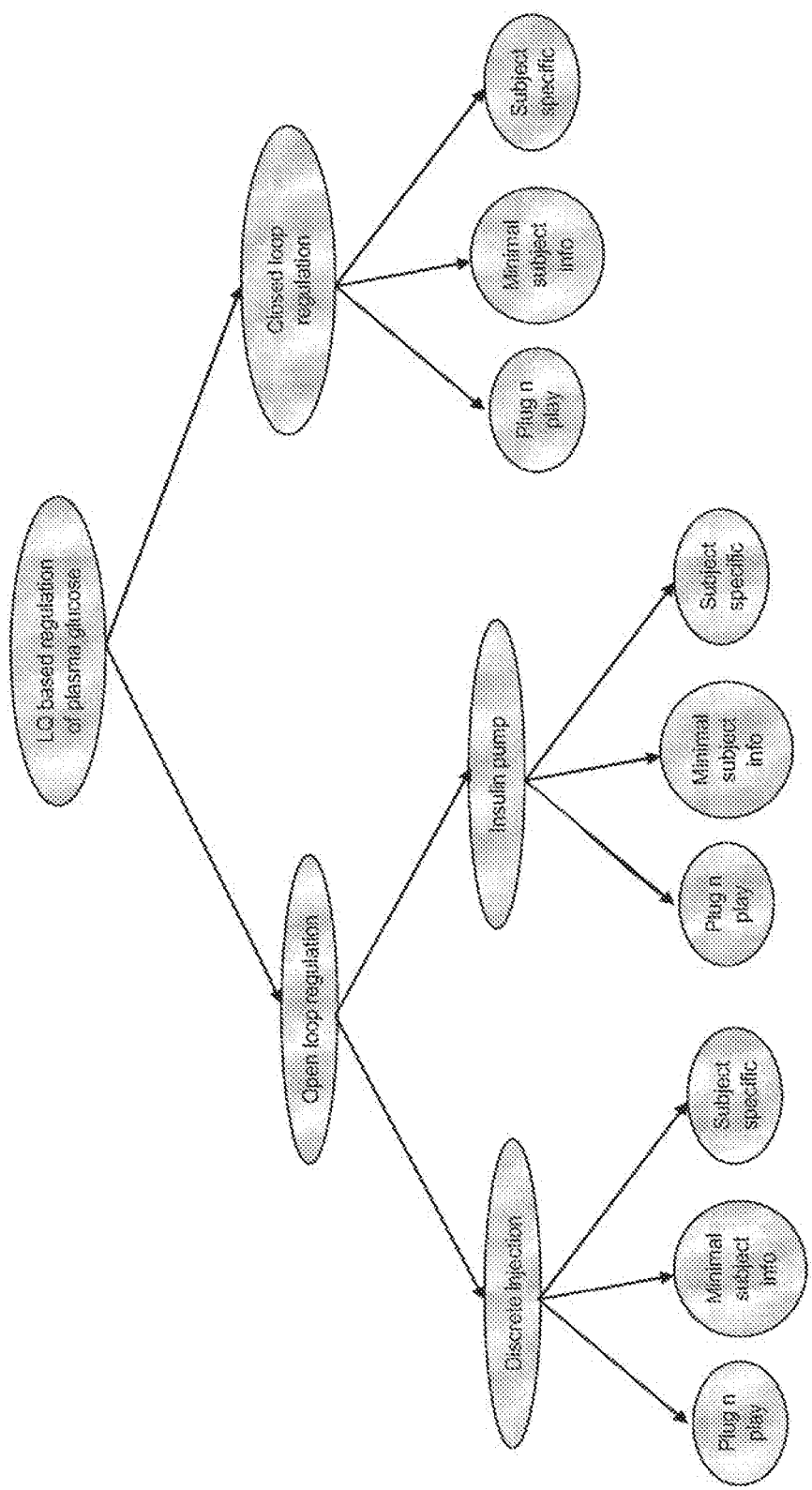
FIG. 4: shows a hierarchical diagram of application of the LQG based glucose regulation method, organized by level of generalization.

The methods and Artificial Pancreas Control Systems of the present invention can be employed in at least three different fields of application of the LQ-based regulator (See, FIG. 4):

(i) computation of optimal boluses for isolated injection insulin treatments (meal and correction boluses), (ii) open loop control using an insulin pump, where the user is advised on pre-meal boluses and basal rate changes, and (iii) closed loop glucose control, where the sensor is automatically linked with insulin pump via the algorithm, with only safety oversight by the user.

Each application requires different settings of the method and restrict the use of some of the modules presented above, either because they cannot be applied, or because they are sub-optimal or could be harmful. In this section we review each application field, describing possible implementation and module restrictions.

Bolus treatment: injection or insulin pen—type device: The main characteristic of this application field is the irregular infrequent actuation time. Therefore, there is a need to estimate the effect of insulin over a long period of time, as opposed to open or closed-loop regulation. While the state of the system can be observed almost real-time via the previously presented observer (iterations are triggered by frequently arriving sensor values), patients act on their blood sugar a few times a day (commonly 3 to 5), usually at mealtime and in case of very high blood glucose. One of the characteristic of this type of application is the combination of different versions of synthetic insulin in one injection (long acting and short acting). These characteristics force the following regulator characteristics: (1) observer triggered by arriving sensor data and not only by actuation time; (2) modified injection for boluses (see calculation of the injection above); (3) predicted injection calculation; (4) Minimization of the instantaneous error; and (5) target tracking is not available.

Open-loop control: patient operated pump: Open-loop control refers to moderately frequent potentially irregular actuation of insulin treatment via an insulin pump capable of delivering basal_rate and boluses, where the regulator does not control the pump automatically but instead advises the patient on the amount and the timing of insulin doses. For irregular-actuation implementation a monitoring system should be added to the observer to alarm the user that action is needed, for example if the predicted glucose concentration does not come back to target within reasonable time. (1) observer triggered by arriving sensor data and not only by actuation time; (2) modified injection for boluses (see calculation of the injection above); (3) subtraction of basal rate from injection scheme; (4) possibility of regular actuation schedule of several hours (during the day); (5) predicted injection calculation; and (6) minimization of the instantaneous error.

Figure 5:
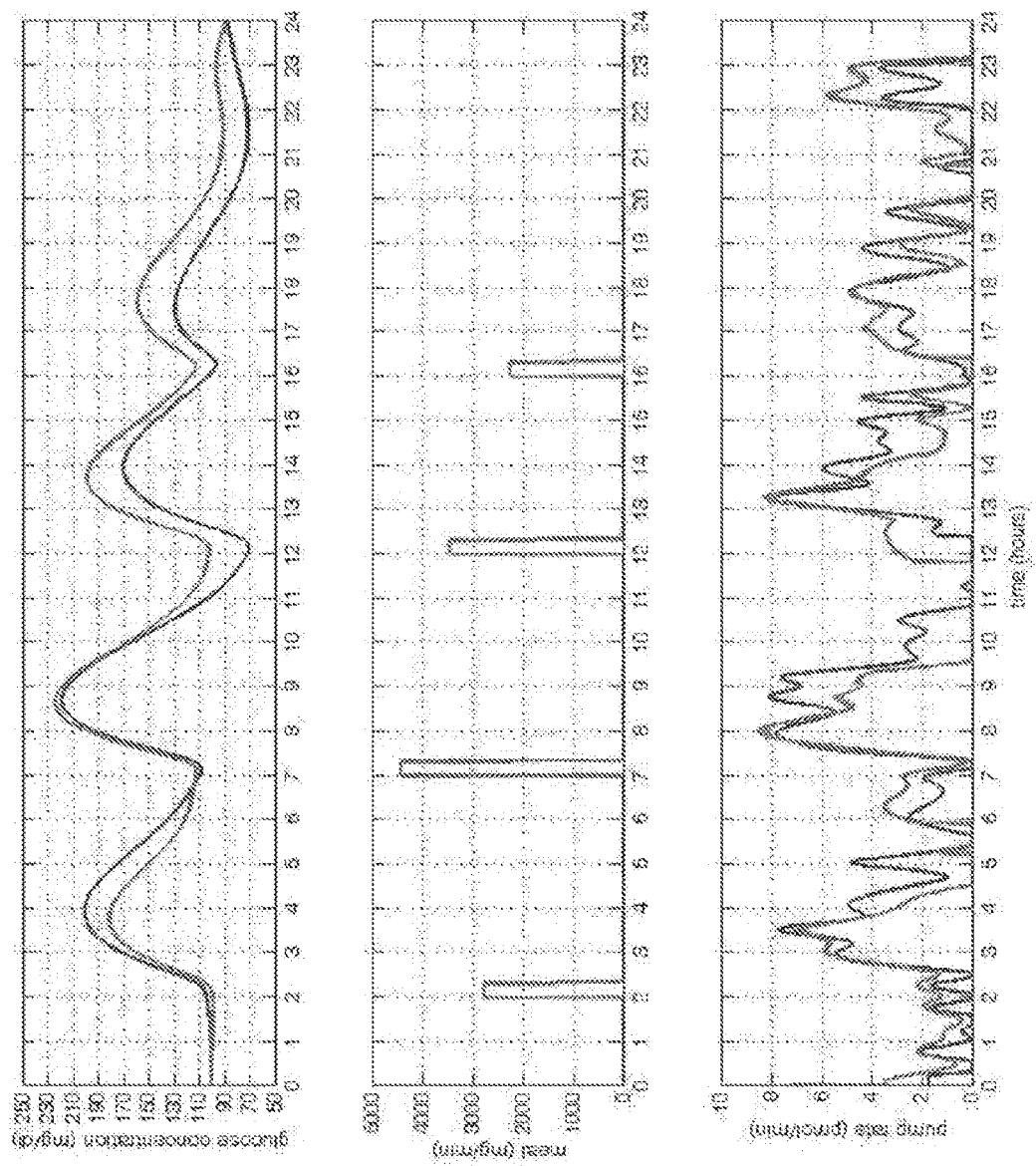
FIG. 5: shows a simulation of automatic control using SC sensor with 1 minute actuation time, standard Kalman Filter, predictive actuation.

Closed-loop control refers to insulin treatment via an insulin pump where actuation is automatically transmitted from the algorithm to the pump. It this particular case actuation is regular and frequent. The user maintains oversight over the insulin amount injected. In this particular application all the proposed modules are applicable, and the actuation frequency can be optimized for minimal energy expenditure of the pump. Simulation provides insight into such control as shown in FIG. 5, which shows a simulation of automatic control using SC sensor with 1 minute actuation time, standard Kalman Filter, predictive actuation.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

What is claimed is:

1. A computer-implemented method for determining an insulin dosing recommendation, the method comprising:

applying, by a processor, an adaptive observer scheme to estimate a present physiological state of a patient based on at least one measurement of blood glucose concentration in the patient, wherein the adaptive observer scheme models the present physiological state of the patient using a dynamic model;

applying, by a processor, the estimated physiological state to a Linear Quadratic regulator to determine an insulin dosing recommendation based on the estimated present physiological state and past physiological state estimations, and outputting, by a processor, the insulin dosing recommendation to a user to determine an appropriate insulin injection to be administered to said patient.

2. A computer-implemented method for determining an insulin dosing recommendation comprising:

applying, by a processor, an adaptive observer scheme to estimate a present physiological state of a patient based on at least one measurement of blood glucose concentration in the patient, wherein the adaptive observer scheme models the present physiological state of the patient using a dynamic model;

applying, by a processor, the estimated physiological state to a Linear Quadratic regulator to determine an insulin dosing recommendation based on the estimated present physiological state and past physiological state estimations, and outputting, by a processor, the insulin dosing recommendation to a user to determine an appropriate insulin injection to be administered to said patient, wherein the dynamic model is one of:

a minimal model of glucose kinetics (MMGK), and wherein the MMGK is augmented to take into account transport of insulin from an injection site to central circulation, as well as transport of glucose from the patient's stomach to central circulation;

a reduced meal model (RMM), and wherein the RMM is augmented using two subcutaneous insulin equations, an interstitial glucose equation, and modeling a meal via a single equation; or an augmented meal model (AMM), which is augmented by two additional insulin states for transport and an additional glucose compartment (interstitium).

3. The method of claim 1, wherein the dynamic model employs a plurality of physiological parameters, and wherein the method further comprises an initial step of customizing the dynamic model by fixing at least one physiological parameter.

4. The method of claim 3, wherein at least one physiological parameter is fixed at an average value, wherein the average value represents an average of values measured for a plurality of subjects.

5. The method of claim 2, wherein the dynamic model employs a plurality of physiological parameters, and wherein the method further comprises an initial step of customizing the dynamic model by fixing at least one physiological parameter.

6. The method of claim 1, comprising determining an optimal gain for the dynamic model.

7. The method of claim 1, wherein the dynamic model is optimized using a Kalman filter.

8. The method of claim 1, wherein the dynamic model is optimized using an extended Kalman filter.

9. The method of claim 1, wherein the insulin dosing recommendation is defined as a linear combination of a gain vector (S) and a state vector (X), so as to minimize a quadratic cost function.

10. A computer-implemented method for determining an insulin dosing recommendation to achieve an optimal glycemic control, the method comprising:

taking a measurement of blood glucose concentration in a patient at each of a plurality of actuation times;

applying, by a processor, an adaptive filter scheme at each actuation time to generate an estimate of the patient's present physiological state based on the most recent measurement of blood glucose concentration;

storing, by a processor, the estimate of the patient's present physiological state;

using, by a processor, Linear Quadratic methodology to determine an insulin dosing recommendation based on the estimate of the patient's present physiological state and based on past estimates of the patient's physiological state, outputting, by a processor, the insulin dosing recommendation to a user to determine an appropriate insulin injection to be administered to said patient.

11. The method according to claim 10, wherein the actuation times are spaced at regular intervals of less than 15 minutes.

12. An artificial pancreas control system for determining an insulin dosing recommendation, the system comprising:

an observer, comprising a programmable computer controller programmed to receive real-time measurements of blood glucose concentration in a patient, and to apply an adaptive filter scheme to estimate a present physiological state of a patient based on the measurements of blood glucose concentration; and an LQ Regulator, comprising a second programmable computer controller programmed to receive the present physiological state estimation from the observer, and to use Linear Quadratic methodology to determine the insulin dosing recommendation based on the estimated present physiological state and past physiological state estimations.

13. The artificial pancreas control system according to claim 12, wherein the second programmable computer controller is programmed to present the insulin dosing recommendation to the patient in an open-loop application.

14. The artificial pancreas control system according to claim 12, wherein the second programmable computer controller is programmed to present the insulin dosing recommendation directly to an insulin pump in a closed-loop application.

* * * * *